(12) United States Patent
Kim et al.

(10) Patent No.: US 11,576,651 B2
(45) Date of Patent: Feb. 14, 2023

(54) SWIVEL DEVICE AND MEDICAL APPARATUS INCLUDING THE SAME

(71) Applicant: Siemens Medical Solutions USA, Inc., Malvern, PA (US)

(72) Inventors: NamHoon Kim, Seoul (KR); SeungHoon Kim, Seongnam-si (KR)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1330 days.

(21) Appl. No.: 15/828,943

(22) Filed: Dec. 1, 2017

(65) Prior Publication Data

US 2018/0168547 A1    Jun. 21, 2018

(30) Foreign Application Priority Data

Dec. 19, 2016  (KP) .......................... 10-2016-0173760

(51) Int. Cl.

| | |
|---|---|
| *A61B 8/00* | (2006.01) |
| *F16M 11/06* | (2006.01) |
| *A61B 90/50* | (2016.01) |
| *A61B 50/13* | (2016.01) |
| *A61B 50/33* | (2016.01) |
| *F16M 11/20* | (2006.01) |
| *F16M 11/42* | (2006.01) |
| *F16M 11/08* | (2006.01) |

(52) U.S. Cl.
CPC ............ *A61B 8/4405* (2013.01); *A61B 50/13* (2016.02); *A61B 50/33* (2016.02); *A61B 90/50* (2016.02); *F16M 11/06* (2013.01); *F16M 11/08* (2013.01); *F16M 11/2014* (2013.01); *F16M 11/42* (2013.01); *A61B 8/462* (2013.01); *F16M 11/2007* (2013.01); *F16M 2200/024* (2013.01)

(58) Field of Classification Search
CPC .. F16M 11/06; F16M 11/08; F16M 2200/021; F16M 2200/024; F16M 11/2014; F16M 2200/08; F16M 11/10; A61B 50/13; A61B 8/00; A61B 8/44; A61B 8/4405; F16H 1/04; F16H 1/06
See application file for complete search history.

(56) References Cited

U.S. PATENT DOCUMENTS

| | | | | |
|---|---|---|---|---|
| 1,902,282 | A | * | 3/1933 | Hultgren ............ B61D 33/0085 248/425 |
| 4,254,319 | A | * | 3/1981 | Beh ...................... H05B 6/6411 219/755 |
| 4,297,548 | A | * | 10/1981 | Little ..................... H01H 35/00 200/61.4 |
| 4,736,217 | A | * | 4/1988 | McDowell ............. F16M 13/00 396/428 |
| 5,129,397 | A | * | 7/1992 | Jingu ....................... A61B 8/00 600/437 |
| 6,027,257 | A | * | 2/2000 | Richards ................ F16M 11/18 396/428 |

(Continued)

FOREIGN PATENT DOCUMENTS

| | | |
|---|---|---|
| CN | 102160802 | 8/2011 |
| CN | 202834606 | 3/2013 |

(Continued)

*Primary Examiner* — Christopher Garft

(57) ABSTRACT

A swivel device includes a base, a first gear fixed to the base, a tray configured to relatively rotate with respect to the base, a second gear fixed to the tray and engaged with the first gear so as to rotate together with the tray wherein the second gear has a smaller diameter than the first gear, a stopper wheel coaxially fixed to the second gear, and a stopper configured to stop rotation of the stopper wheel to fix a position of the tray.

14 Claims, 11 Drawing Sheets

(56) References Cited

U.S. PATENT DOCUMENTS

| | | | |
|---|---|---|---|
| 6,648,825 B1 | 11/2003 | Mesaros | |
| 6,709,391 B2 | 3/2004 | Mesaros | |
| 7,407,143 B1* | 8/2008 | Chen | B60R 11/0241 248/316.4 |
| 9,200,749 B2* | 12/2015 | Song | F16M 13/022 |
| 9,504,447 B2* | 11/2016 | Messina | H01H 9/161 |
| 2003/0042772 A1* | 3/2003 | Park | A61B 1/00048 297/217.1 |
| 2004/0184223 A1* | 9/2004 | Yeh | G06F 1/1632 361/600 |
| 2007/0247977 A1* | 10/2007 | Kaneko | F16M 11/18 368/190 |
| 2009/0154083 A1* | 6/2009 | Katsumata | F16M 11/046 361/679.07 |
| 2009/0314912 A1* | 12/2009 | Whitley | F16M 11/16 248/299.1 |
| 2011/0130782 A1 | 6/2011 | Kan et al. | |
| 2012/0067149 A1* | 3/2012 | Yoon | F16M 11/08 74/414 |
| 2013/0030292 A1 | 1/2013 | Nakajima | |
| 2015/0342562 A1* | 12/2015 | Messina | F16M 11/2014 248/124.1 |

FOREIGN PATENT DOCUMENTS

| | | |
|---|---|---|
| CN | 202843641 | 4/2013 |
| CN | 104135940 | 11/2014 |
| CN | 204706626 | 10/2015 |
| KR | 100874391 B1 | 12/2008 |
| KR | 101565109 B1 | 11/2015 |

* cited by examiner

SWIVEL DEVICE AND MEDICAL APPARATUS INCLUDING THE SAME

BACKGROUND

The present disclosure relates to a swivel device and a medical apparatus including the same and, more particularly, to a swivel device which adjusts a rotation stop angle of a tray.

SUMMARY

An ultrasound diagnostic apparatus is an apparatus which non-invasively obtains an image of a cross section of soft tissue or an image of a blood flow by irradiating an ultrasound signal from a body surface of a subject toward a target region within a body and extracting information from a reflected ultrasound signal.

As compared with other imaging diagnosis apparatuses such as an X-ray examination apparatus, a computerized tomography (CT) scanner, a magnetic resonance image (MRI) scanner, a nuclear medical examination apparatus and the like, the ultrasound diagnostic apparatus has advantages in that it is small in size, low-priced, capable of displaying an image in real time, and high in safety due to lack of exposure to X-rays or the like. Thus, the ultrasound diagnostic apparatus is widely used for diagnosis of the heart, abdominal organs, urinary system, and reproductive organs.

The ultrasound diagnostic apparatus includes a cart-type main body configured to accommodate major components and a probe connected to the main body and configured to transmit and receive an ultrasound wave. In addition, the ultrasound diagnostic apparatus further includes a control panel and a display installed on the main body.

The control panel is installed at the front portion of the main body and includes various switches and operation keys for inputting commands required for operations. Further, the display is installed at the upper portion of the main body and displays ultrasound wave diagnosis results as images.

For enhancing the convenience of users, such control panel and display may be configured so that they can move up and down in a vertical direction or rotate in a transverse direction.

The control panel may be rotatably installed in the main body along a transverse direction by using a swivel device. The swivel device is provided between the control panel and the main body to rotatably couple the control panel to the main body, such that even though the main body is fixed in place, the control panel can be rotated as necessary to allow adjusting the orientation of the control panel.

Embodiments of the present disclosure provide a swivel device which is capable of solving the aforementioned problems and has a reduced rotation stopping angle.

Furthermore, embodiments of the present disclosure provide a medical apparatus on which such a swivel device is installed to control a control panel.

According to one embodiment of the present disclosure, a swivel device may include: a base; a first gear fixed to the base; a tray configured to relatively rotate with respect to the base; a second gear fixed to the tray and engaged with the first gear so as to rotate together with the tray, the second gear having a diameter smaller than the first gear; a stopper wheel coaxially fixed to the second gear; and a stopper configured to stop rotation of the stopper wheel to fix a position of the tray.

The stopper wheel may include a plurality of grooves configured to define a plurality of rotation stop angles.

The stopper wheel may be configured to rotate according to movement of the tray in a lateral direction.

The tray and the second gear may be configured to rotate in the same direction.

The stopper may be fixed in the tray, and may include a hook configured to engage with at least one of the grooves and a wire configured to cause the hook to engage with or disengage from at least one of the grooves.

A gear ratio of the first gear to the second gear may be from 4:1 to 5:1.

The rotation stop angles may be between 4 degrees and 6 degrees.

The first gear may include teeth formed on an outer circumferential surface of the first gear, and the second gear may be configured to revolve along the outer circumferential surface of the first gear.

The first gear may include teeth formed on an inner circumferential surface of the first gear, and the second gear may be configured to revolve along the inner circumferential surface of the first gear.

The tray and the second gear may be configured to rotate in the opposite direction.

The first gear may have an arc shape.

According to another embodiment of the present disclosure, a medical apparatus may include: a main body including a medical diagnostic device; a display configured to display an operation of the main body; a control panel configured to relatively rotate with respect to the main body; a first gear fixed to the main body; a second gear engaged with the first gear and rotatably fixed to the control panel, the second gear having a diameter smaller than the first gear; a stopper wheel coaxially fixed to the second gear; and a stopper configured to stop rotation of the stopper wheel to fix a position of the control panel.

The medical diagnostic device may be one of an X-ray device, an ultrasound device, or a digital imaging device.

A rotation stop angle of the stopper wheel may be adjusted according to a gear ratio of the first gear to the second gear.

The stopper wheel may have a diameter larger than a diameter of the second gear.

According to one embodiment of the present disclosure, the rotation stop angle of the tray with respect to the base may be reduced by using a reduction gear in the swivel device.

In addition, in the case of applying the swivel device to a medical apparatus, the rotation stop angle of the control panel may be reduced.

BRIEF DESCRIPTION OF DRAWINGS

The following drawings attached thereto illustrate some preferred embodiments of the present disclosure and serve to facilitate understanding of the technical ideas of the present disclosure together with the detailed description of the present disclosure. Thus, the present disclosure should not be construed to be limited to the matters shown in the drawings.

DETAILED DESCRIPTION

Figure 1:
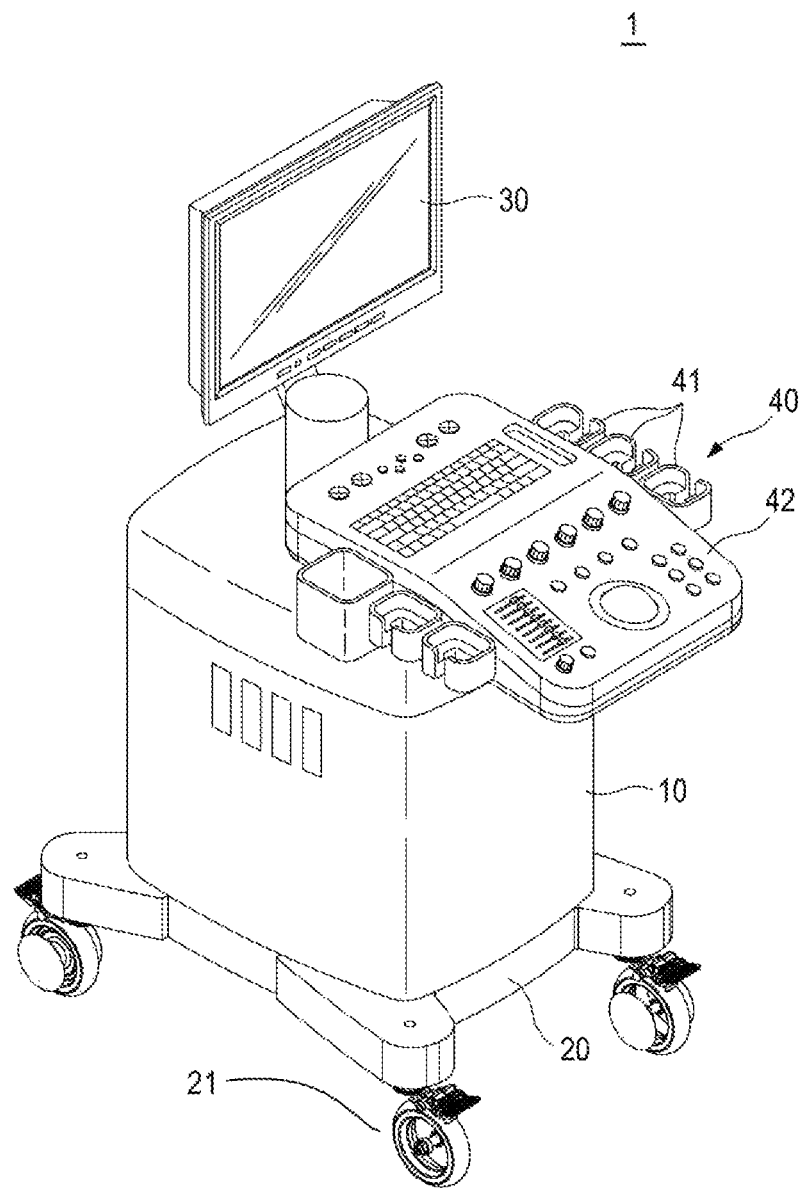
FIG. 1 is a perspective view showing a medical apparatus according to one embodiment of the present disclosure.

Embodiments will now be described in detail with reference to the exemplary drawings. It should be noted that when designating the components of the respective drawings with reference numerals, the same components are designated by like reference numerals as far as possible even if the components are shown in different drawings. Furthermore, in the description of embodiments, if it is determined that the detailed description of well-known components or functions may hinder the understanding of the embodiments, the detailed description will be omitted.

In describing the components of embodiments, terms such as first, second, A, B, (a), (b) and the like may be used. Such terms are intended to merely distinguish one component from another component. The nature, sequence or order of the relevant component is not limited by the terms. When there is a description that one component is "connected" or "coupled" to another component, it is to be understood that one component may be directly connected or coupled to another component, or a third component may be "connected" or "coupled" between the respective components.

Figure 2:
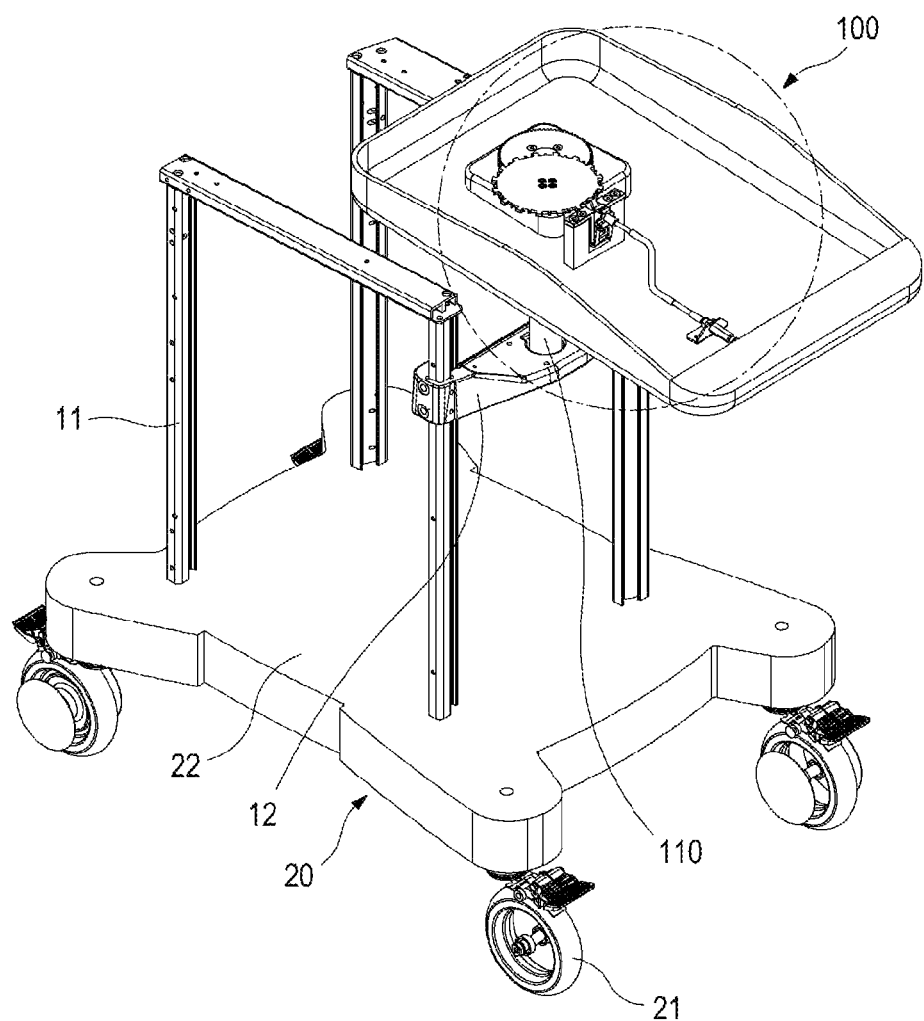
FIG. 2 is a perspective view showing a framework of a medical apparatus including a swivel device according to one embodiment of the present disclosure.

FIG. 1 is a perspective view showing a medical apparatus 1 according to one embodiment of the present disclosure. FIG. 2 is a perspective view showing a framework of a medical apparatus 1 including a swivel device 100 according to one embodiment of the present disclosure.

The medical apparatus 1 may include a cart 20 equipped with a plurality of wheels 21, a medical diagnostic device 10 installed on the cart 20, a display 30 configured to display information transmitted from the medical diagnostic device 10, and a control panel 40 capable of relatively rotating with respect to the medical diagnostic device 10.

The medical diagnostic device 10 may be, for example, one of an X-ray device, an ultrasound device, or a digital imaging device. The medical diagnostic device 10 is not limited to the aforementioned devices but may be a surgical device or a combination of a surgical device and a medical diagnostic device.

The wheels 21 may be installed in the cart 20. The wheels 21 enable the movement of the medical apparatus 1 as a whole. In order to enable the cart 20 to move in any direction parallel to a ground surface, the wheels 21 may rotate about fixed shafts thereof.

In the control panel 40, a keyboard 42 may be installed for inputting commands to the patient diagnostic device 10 and one or more holders 41 for holding probes which make direct contact with a patient to perform diagnosis.

A swivel device 100 to be described later with reference to FIG. 2 is installed in the control panel 40 and the medical diagnostic device 10. A user may control a relative rotation stop angle of the control panel 40 with respect to the medical diagnostic device 10 according to the operation of the swivel device 100.

Referring to FIG. 2, a framework of the medical apparatus 1 equipped with the swivel device 100 is shown. FIG. 2 shows a state in which the medical diagnostic device 10, the display 30, and the control panel 40 are removed from the medical apparatus 1 shown in FIG. 1.

The cart 20 may include a platform 22 installed on the wheels 21 and a frame 11 extending in a direction perpendicular to the platform 22. The medical diagnostic device 10 may be installed on and fixed to the frame 11.

A support stand 12 may be installed at one side of the frame 11. The support stand 12 may fix a position of the swivel device 100. The position of the support stand 12 may be adjusted along a longitudinal direction of the frame 11. As a result, the height position of the swivel device 100 may be adjusted. The lower end portion of a base 110 for the swivel device 100 may be fixed in a position near the center of the support stand 12.

Figure 3:
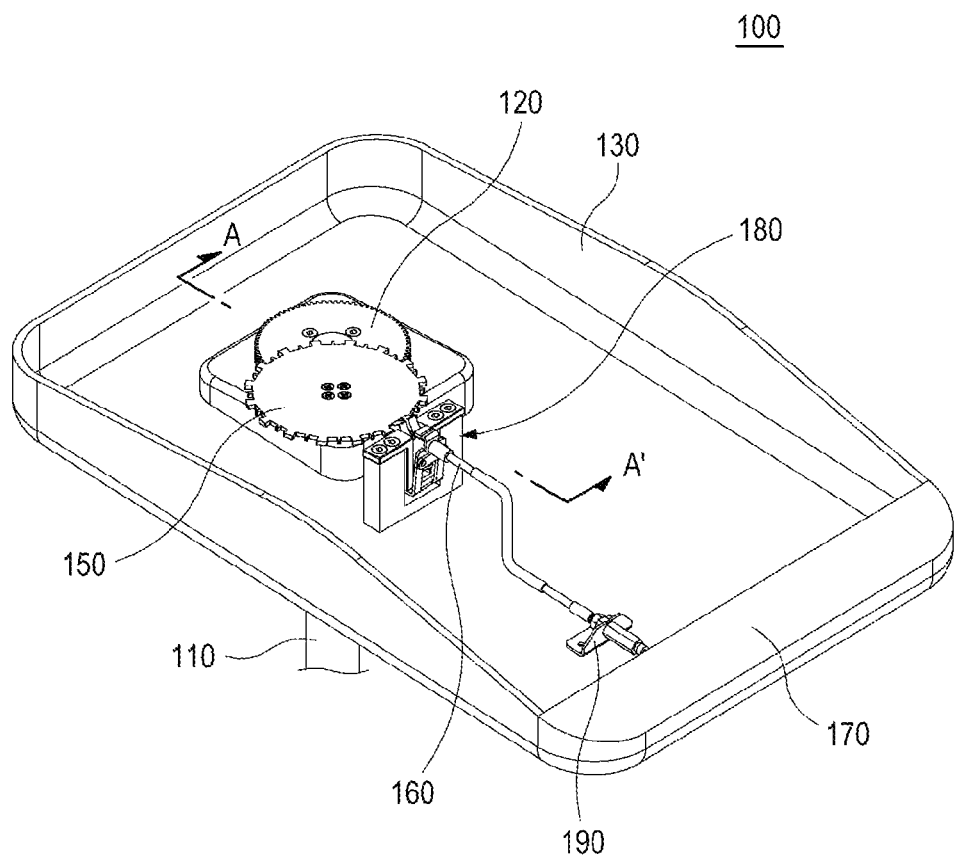
FIG. 3 is a perspective view showing a swivel device according to one embodiment of the present disclosure.
Figure 4:
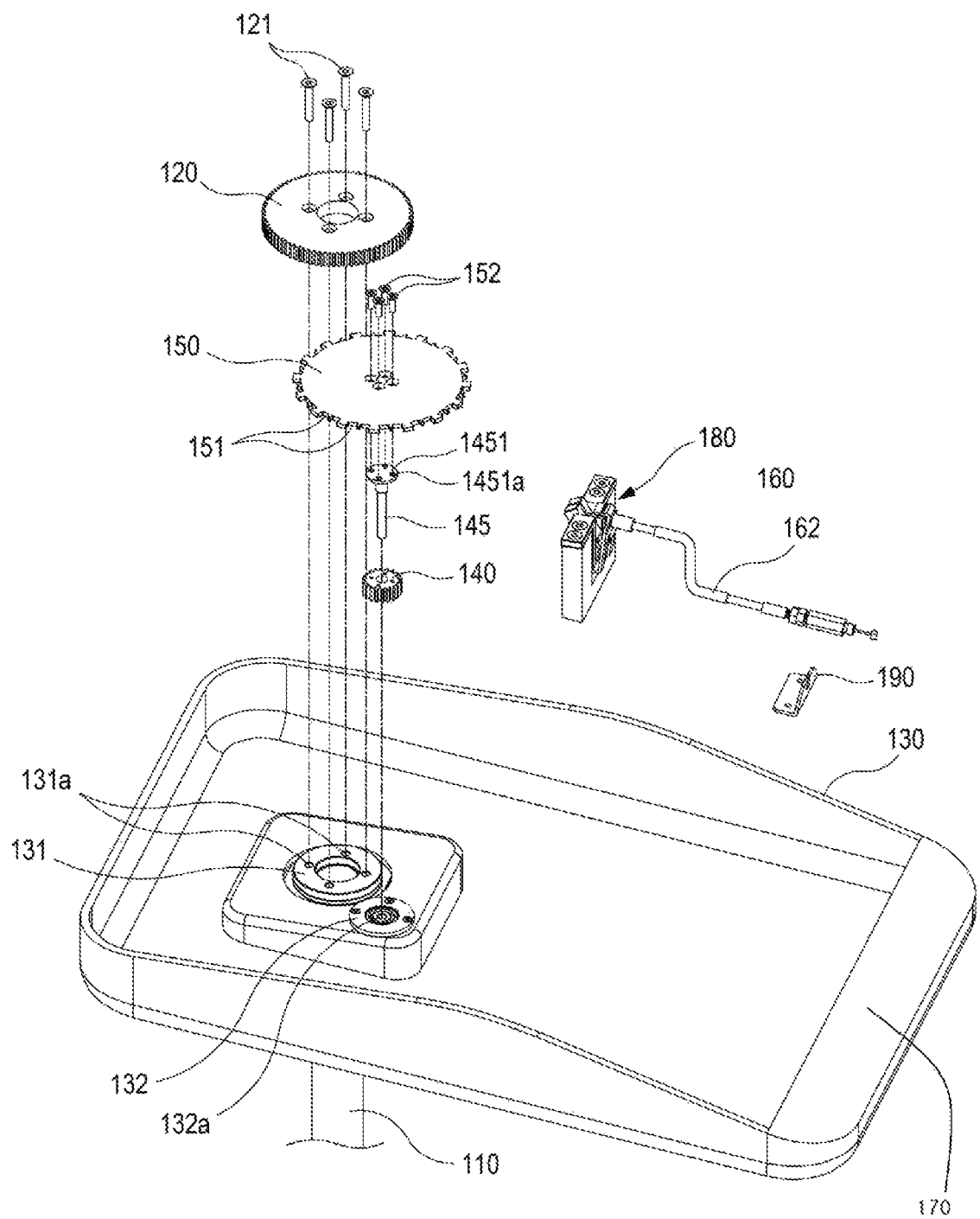
FIG. 4 is an exploded perspective view showing a disassembled state of a swivel device according to one embodiment of the present disclosure.
Figure 5:
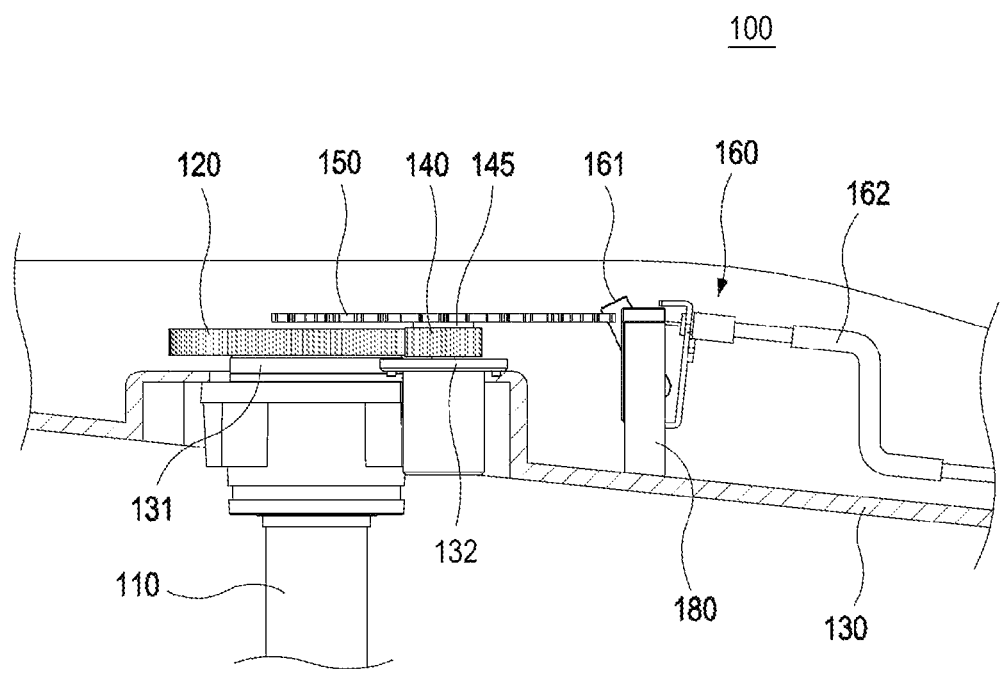
FIG. 5 is a cross-sectional view of the swivel device taken along line A-A' in FIG. 3.
Figure 6:
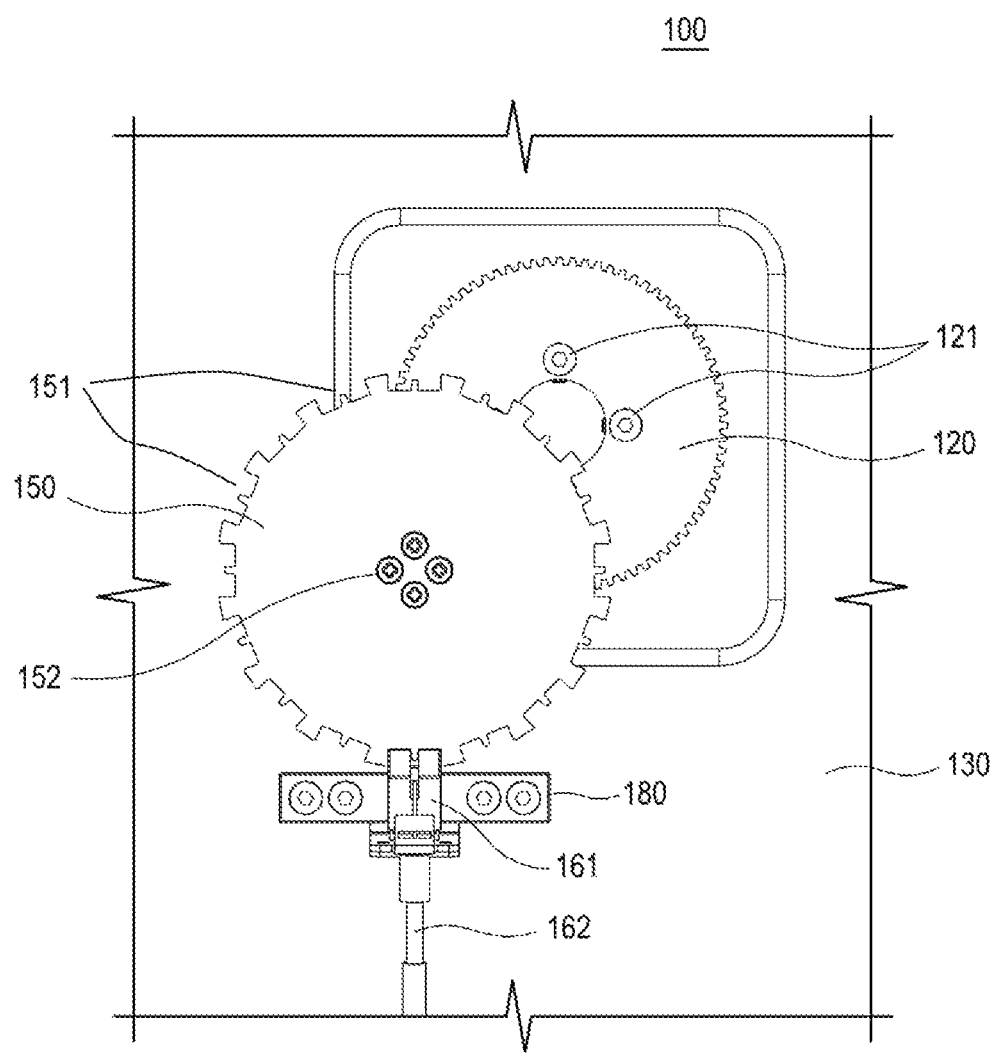
FIG. 6 is a top view of the swivel device shown in FIG. 3.

FIG. 3 is a perspective view showing the swivel device 100 according to one embodiment of the present disclosure. FIG. 4 is an exploded perspective view showing a disassembled state of the swivel device 100. FIG. 5 is a cross-sectional view of the swivel device 100 taken along line A-A' in FIG. 3. FIG. 6 is a top view of the swivel device 100 shown in FIG. 3.

The swivel device 100 may include the base 110, a first gear 120 fixed to the base 110, a tray 130 capable of relatively rotating with respect to the base 110, a second gear 140 fixed to the tray 130 and engaged with the first gear 120 so that the second gear 140 can rotate together with the tray 130 wherein the second gear 140 has a diameter smaller than the first gear 120, a stopper wheel 150 coaxially fixed to the second gear 140, and a stopper 160 configured to stop rotation of the stopper wheel 150 to fix the position of the tray 130.

The base 110 may have, for example, a cylindrical shape or a beam shape, in order to keep the tray 130 spaced apart from the patient diagnostic device 10 by a specified height. Further, the tray 130 may be rotatably held on the base 110. The tray 130 may relatively rotate with respect to the base 110.

Referring to FIGS. 3 and 4, the first gear 120 is immovably fixed to an upper end portion of the base 110. A first fixing plate 131 for fixing the second gear 140 may be installed at the upper end of the base 110. Four bolts 121 may sequentially pass through a plurality of holes formed in the first gear 120 and a plurality of holes 131a formed in the first fixing plate 131 to fix the first gear 120 to the first fixing plate 131.

The first gear 120 may, for example, have the form of a spur gear and may include a plurality of teeth uniformly distributed along the entire outer circumference thereof.

The second gear 140 is fixed to a lower side of the stopper wheel 150 in a coaxial relationship with the stopper wheel 150. The second gear 140 may be, for example, a spur gear having the same gear teeth as those of the first gear 120 so that the second gear 140 can engage with the first gear 120.

A rotary shaft 145 may rotatably fix the second gear 140 and the stopper wheel 150 with respect to the tray 130. The stopper wheel 150 is fixed to an upper end of the rotary shaft 145. The second gear 140 is fitted to the outer circumferential surface of the rotary shaft 145. The rotary shaft 145 may be inserted into a hole 132a formed at the center of a second fixing plate 132 installed on the tray 130.

In order to rotate the stopper wheel 150 and the second gear 140 at the same angle with each other, a third fixing plate 1451 may be disposed at the upper end of the rotary shaft 145. A plurality of stopper bolts 152 may sequentially pass through a plurality of holes formed in the stopper wheel 150, a plurality of holes 1451a formed in the third fixing plate 1451, and a plurality of holes formed in the second gear 140. Thus, the relative rotation of the stopper wheel 150 and the second gear 140 may be restrained by the stopper bolts 152.

Referring to FIG. 5, the tray 130 is held in a gap between the first gear 120 and the base 110. Therefore, the tray 130 may rotate without interference of the first gear 120 and the base 110. The length of the gap may be set to be substantially equal to or a little larger than the thickness of the tray 130. As a result, the tray 130 can rotate without shaking and thus can stably rotate without unnecessary up and down movement.

Referring to FIG. 6, a plurality of grooves 151 defining a plurality of rotation stop angles may be formed in the stopper wheel 150. For example, sixteen grooves 151 may be formed in the stopper wheel 150. In this case, the angle between two adjacent grooves 151 may be about 22.5 degrees. A larger number of grooves 151 may be formed as the size of the tray 130 increases to the extent allowed by the size limitation.

A reduction gear set may include the first gear 120, the second gear 140, and the stopper wheel 150. For example, the first gear 120 may be larger than the second gear 140. The diameter of the stopper wheel 150 may be substantially equal to or larger than the diameter of the first gear 120.

For example, the second gear 140 may be a gear having a small diameter equal to about ¼ to ⅕ of the diameter of the first gear 120. Thus, the gear ratio of the first gear 120 to the second gear 140 may be approximately 4:1 to 5:1.

The control panel 40 may be installed on the tray 130. When the medical apparatus 1 is used by a user, there may be a need to rotate the control panel 40 under various circumstances. Various angles may be required for the rotation stop angles of the control panel 40 depending on the types of devices or the intended use.

According to one embodiment, the reduction gear set 120, 140, and 150 described above is installed in the swivel device 100. Thus, the rotation stop angle of the control panel 40 may be reduced. Further, since the rotation stop angle of the control panel 40 corresponds to the rotation stop angle of the stopper wheel 150, the rotation stop angle of the stopper wheel 150 may be adjusted according to the gear ratio of the first gear 120 to the second gear 140.

The stopper 160 is fixed on the tray 130. The stopper 160 may include a hook 161 for engaging with at least one of the plurality of grooves 151 and a wire 162 for causing the hook 161 to engage with or disengage from at least one of the grooves 151.

The rotation of the stopper wheel 150 may be stopped by the stopper 160. The stopper 160 may be spaced apart above the tray 130 by a stand 180. A holder 190 is installed between the stand 180 and the tray 130. The holder 190 may fix the wire 162 extending in an elongated manner.

Referring again to FIGS. 4 and 5, the wire 162 may extend from the hook 161 to a trigger 170. As a user presses the trigger 170, the trigger 170 moves the wire 162, thereby causing the hook 161 to disengage from the stopper wheel 150. In contrast, when the trigger 170 is not pressed by a user, the hook 161 is engaged with a groove 151 and thus may stop rotation of the stopper wheel 150.

Figure 7:
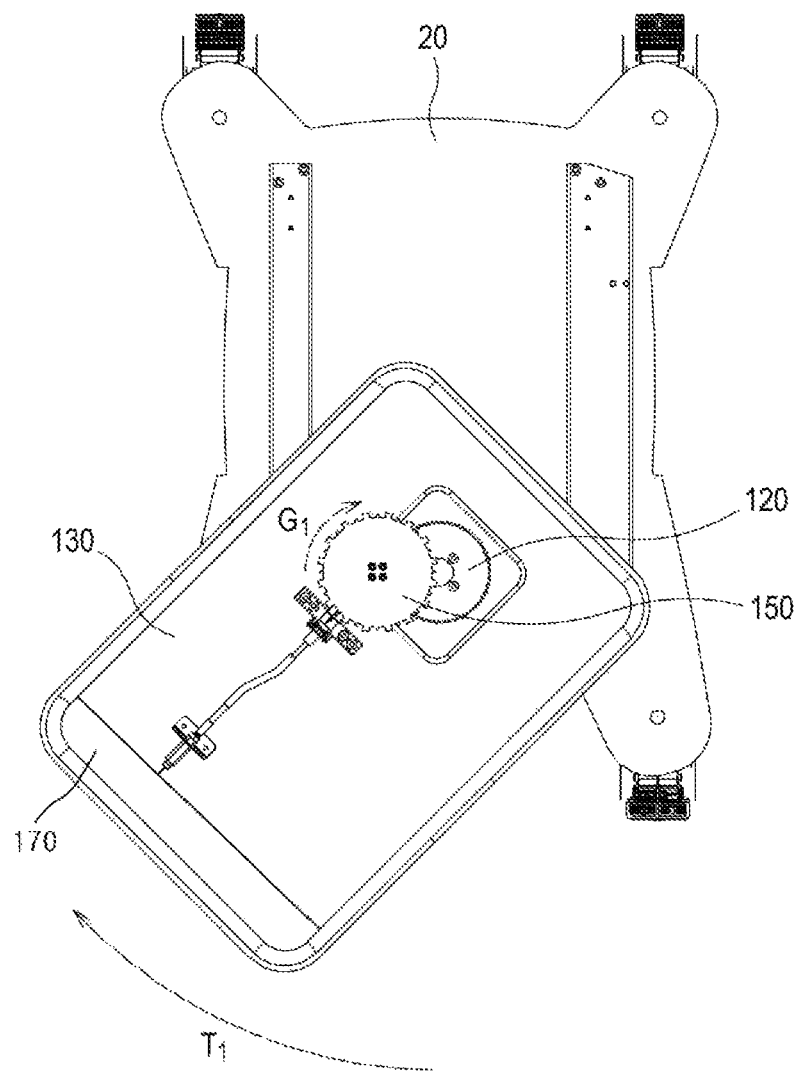
FIG. 7 is an operation view showing a state in which the swivel device shown in FIG. 3 is operated in one direction.
Figure 8:
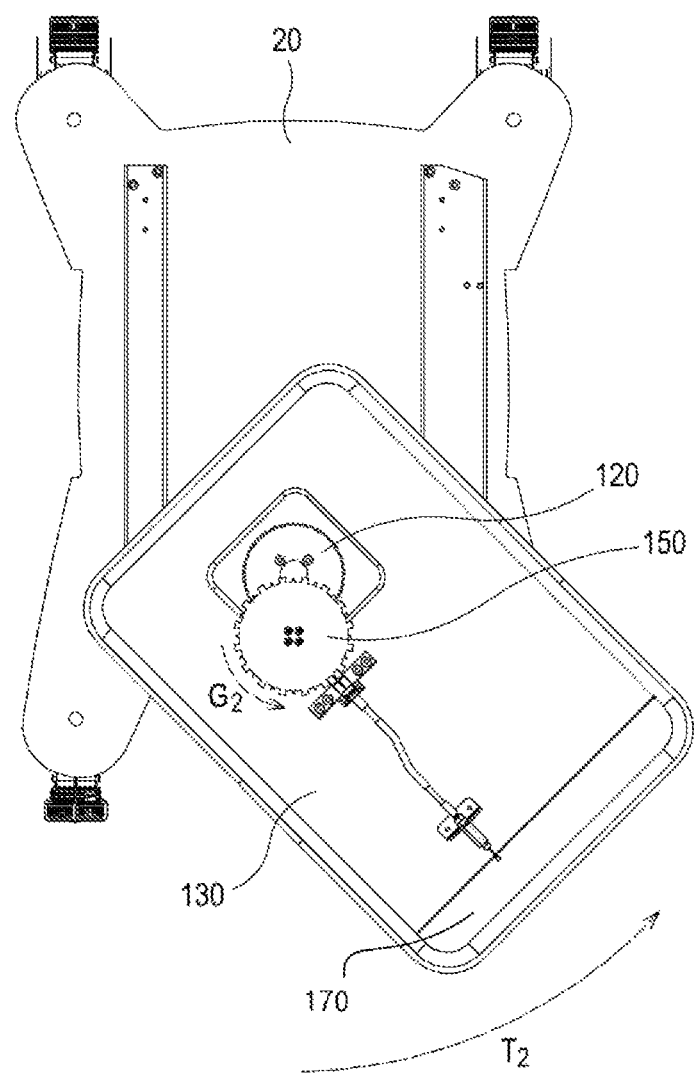
FIG. 8 is an operation view showing a state in which the swivel device shown in FIG. 3 is operated in the other direction.

FIG. 7 is an operation view showing a state in which the swivel device 100 shown in FIG. 3 is operated in one direction. FIG. 8 is an operation view showing a state in which the swivel device 100 shown in FIG. 3 is operated in the other direction.

In order for a user to rotate the tray 130, a force may be applied to the tray 130 in a lateral direction in a state where the trigger 170 is pressed. At this time, as the tray 130 rotates in a lateral direction, the stopper wheel 150 may also rotate. Since the second gear 140 is coaxially installed with the stopper wheel 150, the rotation angle of the stopper wheel 150 corresponds to the rotation angle of the second gear 140.

The gear teeth of the first gear 120 are formed on the outer circumferential surface of the first gear 120. The second gear 140 may revolve along the outer circumferential surface of the first gear 120. Since the second gear 140 revolves along the outer circumferential surface of the first gear 120, the rotation direction of the tray 130 is the same as the rotation direction of the second gear 140.

Specifically, when the tray 130 is rotated in a first direction T1, the second gear 140 may also rotate in a first direction G1. In contrast, when the tray 130 is rotated in a second direction T2, the second gear 140 may also rotate in a second direction G2.

In the case where the gear ratio of the first gear 120 to the second gear 140 is, for example, about 5:1, the rotation stop angle of the tray 130 may be about 5.5 degrees. That is, when the hook 161 moves between the adjacent grooves 151 making an angle of about 22.5 degrees and engages with one of the grooves 151, the tray 130 may be moved by about 5.5 degrees with respect to the base 110.

As another example, when the gear ratio of the first gear 120 to the second gear 140 is, for example, about 9:1, the rotation stop angle of the tray 130 may be 2.5 degrees. That is, when the hook 161 moves between the adjacent grooves 151 making an angle of about 22.5 degrees and engages with one of the grooves 151, the tray 130 may be rotated by 2.5 degrees with respect to the base 110.

In short, the rotation stop angle of the tray 130 may be adjusted according to the gear ratio of the first gear 120 to the second gear 140. Accordingly, given the constraints on the manufacturing environment due to the increase in the gear manufacturing cost, the rotation stop angle of the tray 130 may be set to fall within a range of 4 to 6 degrees.

In the case without the aforementioned reduction gear set 120, 140 and 150, the tray 130 may rotate with respect to the center of the base 110 as a rotation axis. In this case, the angle between the grooves 151 of the tray 130 inevitably becomes a rotation stop angle. In the design process, since constraints on the size of the tray 130 exist, there is a limit in reducing the rotation stop angle by increasing the size of the stopper wheel 150.

In contrast, the swivel device 100 according to one embodiment makes use of the reduction gear set 120, 140 and 150. Thus, the rotation stop angle can be reduced to ¼ to ⅕ in size by adjusting the gear ratio of the first gear 120 to the second gear 140 without increasing the size of the stopper wheel 150.

Hereinafter, swivel devices 200 and 300 differing in some configurations from the aforementioned swivel device 100 will be described according to other embodiments. The components having the same names perform the same functions. Accordingly, detailed descriptions on the components having the same functions will be omitted. Descriptions will be made by focusing on configurations that are different from each other.

Figure 9:
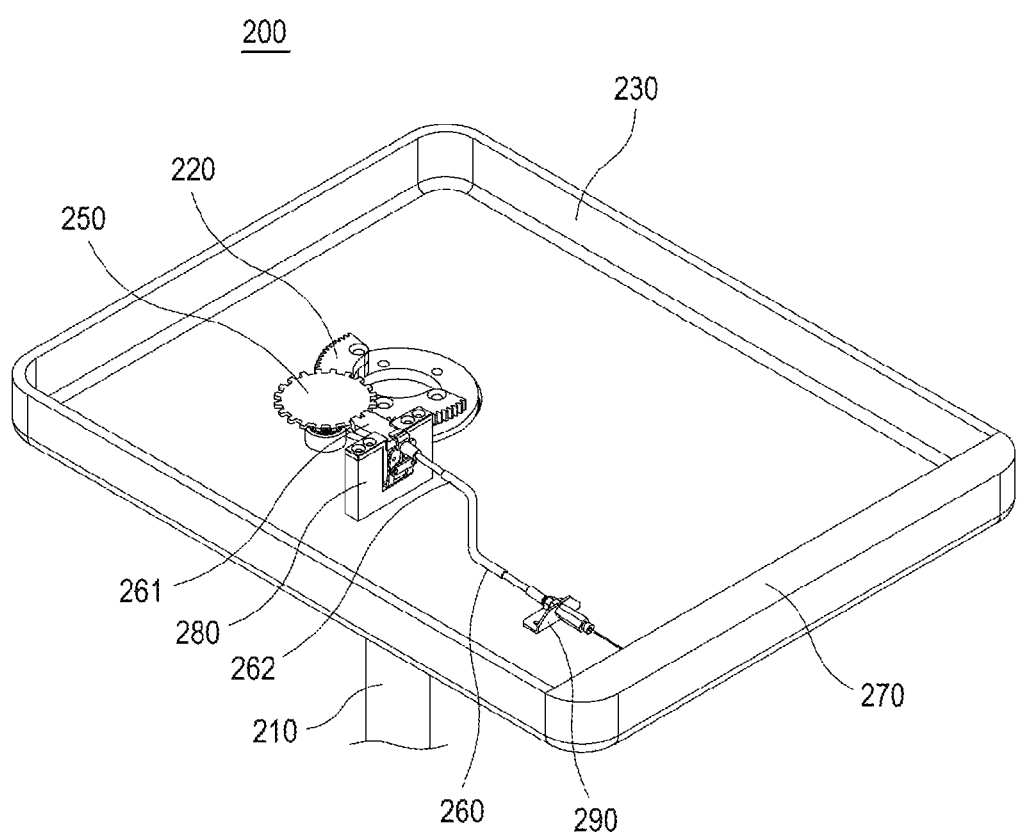
FIG. 9 is a perspective view showing a swivel device according to another embodiment of the present disclosure.

FIG. 9 is a perspective view showing the swivel device 200 according to another embodiment of the present disclosure.

The swivel device 100 may include a first gear 220, a second gear 240, a tray 230, a stopper wheel 250, and a stopper 260. Further, a trigger 270, a stand 280, and a holder 290 or the like may be provided.

A hook 261 may engage with at least one of the grooves of the stopper wheel 250. The hook 261 may engage with or disengage from the stopper wheel 250 by a wire 262.

Unlike the swivel device 100 according to the embodiment described above, the first gear 220 of the swivel device 200 shown in FIG. 9 may have an arc shape. That is, the first gear 220 may not have a circle shape in its entirety but may be formed in a semi-circular shape or a shape of an arc which forms a portion of a circle.

In the medical apparatus 1, the extent of rotation necessary for the control panel 40 about the base 110 may be determined according to the type of the medical diagnostic device 10. According to the foregoing descriptions, the rotation stop angle of the control panel 40 may become smaller as the gear ratio of the first gear 220 to the second gear 240 increases.

Further, as the diameter of the first gear 220 increases, the rotation stop angle of the control panel 40 may decrease.

Accordingly, when the control panel 40 need not be rotated by 360 degrees, it may be possible to use the first gear 220 having an outer circumferential surface formed over an extent corresponding to the required rotation extent of the control panel 40.

For example, the area of the first gear 220 of a quarter arc shape having a central angle of 90 degrees is equal to the area of a entirely circular gear having a diameter which is substantially equal to one half of the diameter of the first gear 220 of a quarter arc shape. In the first gear 220 of a quarter arc shape as compared with the entirely circular gear, the gear ratio of the first gear 220 to the second gear 240 may be doubled and the rotation stop angle may be reduced by half.

Similar to the swivel device 100 described above, even when the first gear 220 has an arc shape, the rotation direction of the tray 230 is the same as the rotation direction of the second gear 240.

Figure 10:
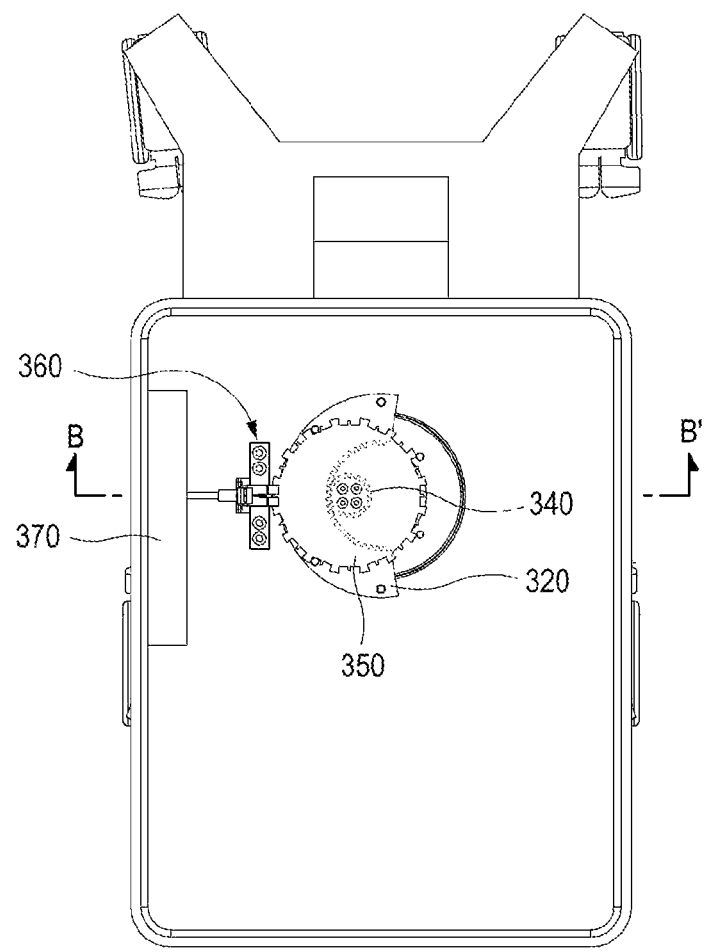
FIG. 10 is a top view showing a swivel device according to a further embodiment of the present disclosure.
Figure 11:
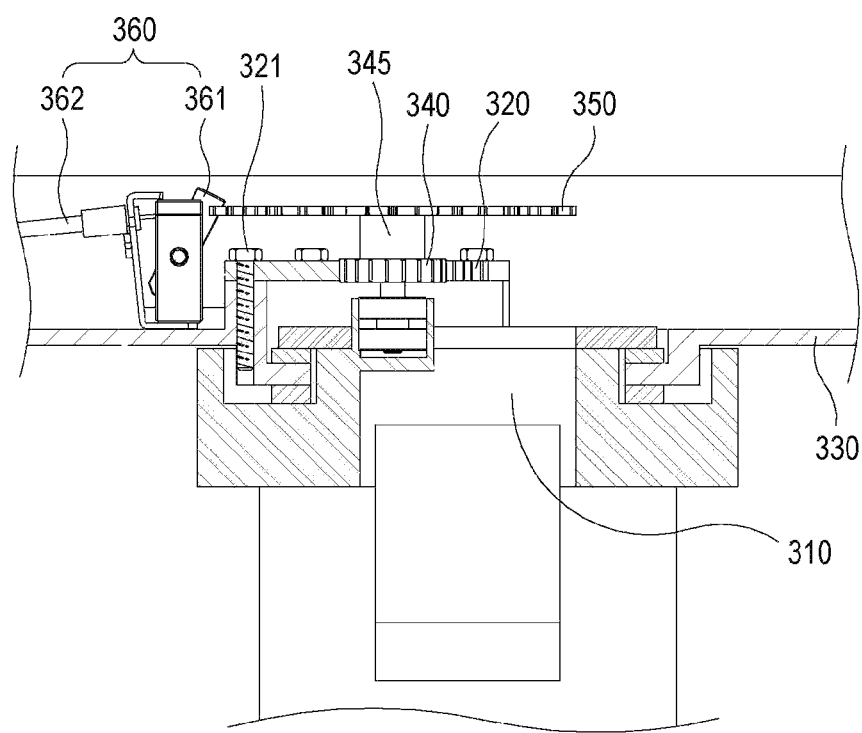
FIG. 11 is a cross-sectional view of the swivel device taken along line B-B' in FIG. 10.

FIG. 10 is a top view showing the swivel device 300 according to a further embodiment of the present disclosure. FIG. 11 is a cross-sectional view of the swivel device 300 taken along line B-B' in FIG. 10.

The swivel device 300 may include a first gear 320, a second gear 340, a tray 330, a stopper wheel 350, and a stopper 360. Further, a trigger 370, a stand 380, a holder 390 or the like may be provided.

The first gear 320 may be fixed to a base 310 by at least one bolt 321. The second gear 340 may be rotatably fixed on the tray 330 by a rotary shaft 345. The second gear 340 and the stopper wheel 350 may be rotated at the same angle.

The gear teeth of the first gear 320 are formed on an inner circumferential surface of the first gear 320. The second gear 340 may revolve along the inner circumferential surface of the first gear 320. Since the second gear 340 revolves along the inner circumferential surface of the first gear 320, the gear teeth of the second gear 340 may engage with the gear teeth of the first gear 320 in a more firm manner by a centrifugal force during the rotation of the tray 330.

Unlike the swivel devices 100 and 200 described above, in the swivel device 300 according to this embodiment, the rotation direction of the tray 330 and the rotation direction of the second gear 340 may be opposite to each other. For example, when the tray 330 is rotated in a clockwise direction, the second gear 340 may rotate in a counterclockwise direction. In contrast, when the tray 330 is rotated in a counterclockwise direction, the second gear 340 may rotate in a clockwise direction.

While some embodiments have been described above using a limited number of drawings, a person having ordinary knowledge in the relevant technical field will be able to derive different changes and modifications from the foregoing descriptions. For example, suitable results may be achieved even when the described techniques are performed in a different order than the described order and/or even when the components of the described structures, devices and the like are coupled or combined in a different form than the described method or replaced or substituted by other components or equivalents. Thus, other implementations, other embodiments and other subject matters equivalent to those of the claims fall within the scope of the claims.

What is claimed is:

1. A swivel device, comprising:
   a base;
   a first gear immovably fixed to the base;
   a tray configured to relatively rotate with respect to the base,
   a second gear fixed to the tray and engaged with the first gear so as to rotate together with the tray, the second gear having a diameter smaller than a diameter of the first gear;
   a stopper wheel coaxially fixed to the second gear; and
   a stopper configured to stop rotation of the stopper wheel to fix a position of the tray, wherein a rotation stop angle of the stopper wheel is adjusted according to a gear ratio of the first gear to the second gear without changing a size of the stopper wheel.

2. The swivel device of claim 1, wherein the base is installed in a medical apparatus.

3. The swivel device of claim 2, wherein the stopper wheel includes a plurality of grooves formed on an outer circumferential surface of the stopper wheel and configured to define a plurality of rotation stop angles.

4. The swivel device of claim 3, wherein the stopper wheel is configured to rotate as the tray moves in a lateral direction.

5. The swivel device of claim 4, wherein the tray and the second gear are configured to rotate in the same direction.

6. The swivel device of claim 3, wherein the stopper is installed on the tray, and the stopper includes a hook configured to engage with at least one of the grooves and a wire configured to cause the hook to engage with or disengage from at least one of the grooves.

7. The swivel device of claim 2, wherein the gear ratio of the first gear to the second gear is from 4:1 to 5:1.

8. The swivel device of claim 3, wherein the rotation stop angles are between 4 degrees and 6 degrees.

9. The swivel device of claim 3, wherein the first gear includes teeth formed on an outer circumferential surface of the first gear, and the second gear is configured to revolve along the outer circumferential surface of the first gear.

10. A medical apparatus, comprising:
    a main body including a medical diagnostic device;
    a display configured to display an operation of the main body;
    a control panel configured to relatively rotate with respect to the main body;
    a first gear immovably fixed to the main body;

a second gear engaged with the first gear and rotatably fixed to the control panel, the second gear having a diameter smaller than a diameter of the first gear;

a stopper wheel coaxially fixed to the second gear; and a stopper configured to stop rotation of the stopper wheel to fix a position of the control panel, wherein a rotation stop angle of the stopper wheel is adjusted according to a gear ratio of the first gear to the second gear without changing a size of the stopper wheel.

11. The medical apparatus of claim 10, wherein the medical diagnostic device is at least one of an X-ray device, an ultrasound device, or a digital imaging device.

12. The medical apparatus of claim 10, wherein the rotation stop angle of the stopper wheel is less than an angle between two adjacent grooves formed on an outer circumferential surface of the stopper wheel.

13. The medical apparatus of claim 10, wherein the stopper wheel has a diameter larger than the diameter of the second gear.

14. The medical apparatus of claim 10 wherein the rotation stop angle of the stopper wheel is reduced to ¼ to ⅕ in size by increasing the gear ratio of the first gear to the second gear to 4:1 to 5:1 without increasing the size of the stopper wheel.

* * * * *